(12) United States Patent
Simon et al.

(10) Patent No.: US 6,838,086 B1
(45) Date of Patent: Jan. 4, 2005

(54) COMPOSITION COMPRISING LOW MOLECULAR WEIGHT HYALURONIC ACID FRAGMENTS

(75) Inventors: Jan Simon, Merzhausen (DE); Stefan Martin, Gundelfingen (DE); Christian Termeer, Freiburg (DE)

(73) Assignee: Universitaetsklinikum Freiburg, Freiburg (DE)

( * ) Notice: Subject to any disclaimer, the term of this patent is extended or adjusted under 35 U.S.C. 154(b) by 0 days.

(21) Appl. No.: 09/763,794

(22) PCT Filed: Aug. 26, 1999

(86) PCT No.: PCT/EP99/06280

§ 371 (c)(1),
(2), (4) Date: Jul. 12, 2001

(30) Foreign Application Priority Data

Aug. 27, 1998 (DE) .......................................... 198 39 113
Nov. 17, 1998 (DE) .......................................... 198 53 066

(51) Int. Cl.$^7$ ........................ A61K 39/00; A01N 65/00; A01N 1/02; C12N 15/63; C12N 15/85
(52) U.S. Cl. ........................ 424/277.1; 424/93.1; 435/2; 435/440; 435/455
(58) Field of Search ........................ 424/277.1, 93.1; 435/2, 455, 440

(56) References Cited

U.S. PATENT DOCUMENTS 4,725,585 A  2/1988  Wenge et al.

FOREIGN PATENT DOCUMENTS

| DE | 44 12 794 A1 | 12/1995 |
| DE | 198 02 540 C1 | 11/1998 |
| JP | 64-000469 | 1/1989 |
| JP | 09-012600 | 1/1997 |
| JP | 09-229930 | 9/1997 |
| WO | WO 97/12633 A1 | 4/1997 |
| WO | WO 97/33592 A1 | 9/1997 |
| WO | WO 98/13382 A1 | 4/1998 |

OTHER PUBLICATIONS

Brand et al (Eur. J. Immunol. May 1998;28(5):1673–1680).*
Haegel–Kronenberger, H. et al., "Regulation of CD44 Isoform Expression and CD44–Mediated Signaling in Human Dendritic Cells", Advances in Experimental Medicine and Biology, 1997, pp. 83–90, No. 417.
Termeer, C. et al., "Dendritic Cell (DC) Maturation by Small Fragments of Hyaluronan (HA) Involves a Highly Specific Nf–01hB and TNF01α–Dependent Pathway", Journal of Investigative Dermatology, Abstracts for the 60th Annual Meeting of the Society for Investigative Dermatology, May 5–9, 1999, pp. 579, vol. 12, No. 4.
Nobel, P. W. et al., "Induction of inflammatory gene expression by low–molecular–weight hyaluronan fragments in macrophages", Chemistry, Biology and Medical Applications of Hyaluronan and Its Derivatives, 1998, pp. 219–225, vol. 72, Wenner–Gren Int. Ser.

* cited by examiner

*Primary Examiner*—G. Nickol
*Assistant Examiner*—C Yaen
(74) *Attorney, Agent, or Firm*—Heller Ehrman White and McAuliffe LLP

(57) ABSTRACT

The invention discloses the use of low molecular weight hyaluronic acid fragments, which can be suitably modified, where appropriate, for producing vaccines. The vaccines are particularly suitable for controlling cancer diseases. Surprisingly, it has been found that low molecular weight hyaluronic acid fragments, which can be suitably modified, where appropriate, can be used both for preparing mature dendritic cells and directly, together with antigens or peptides or carrier systems, as an adjuvant in vaccines. It is likewise possible to couple the low molecular weight hyaluronic acid fragments, which can be suitably modified, where appropriate, to an antigen, peptide or carrier system. The coupled system can then be advantageously employed as a vaccine, in particular for treating cancer diseases.

12 Claims, No Drawings

COMPOSITION COMPRISING LOW MOLECULAR WEIGHT HYALURONIC ACID FRAGMENTS

The invention relates to the use of low molecular weight fragments of hyaluronic acid in immunotherapy, in particular for producing compositions which can be used in immunotherapy. Within the context of this application, such compositions, which can be employed in immunotherapy, are referred to generally as "vaccines".

The preparation of dendritic cells (DC) is gaining ever increasing importance in the therapy of a variety of diseases. The dendritic cells can be used to prepare highly active immunomodulators which can be loaded with a variety of antigens, in particular tumour antigens, virus peptides or compounds having an allergenic effect. These cells are then employed, in adoptive immunotherapy, in patients with tumours or who are suffering from virus diseases or allergies. There is therefore a substantial need in adoptive immunotherapy for dendritic cells, which are preferably to be prepared using standardized, reproducible and inexpensive methods. These methods have to be carried out under GMP/GLP conditions.

A variety of methods for producing dentritic cells from stem cells are known from the prior art.

Haematopoietic stem cells which possess the CD34 surface marker can be isolated from the bone marrow or peripheral blood of chemotherapy patients who have been treated with granulocyte colony-stimulating factor (G-CSF). These stem cells are cultured in the added presence of a variety of cytokines and the dendritic cells are obtained after a relatively long period of culture.

By now, methods have become available for generating dentritic cells in vitro in large numbers from precursor cells present in peripheral blood (J. Immunol. Med. 1996, 196: 137–51; Exp. Hematology 1997, 25: 232–36; Ann. Surgery 1997, 226: 6–16).

While a study carried out on melanoma patients using immature dendritic cells of the prior art shows response rates in 5 out of 16 patients (Nature Medicine 1998, 4: 328–32), it was possible to induce T cells having specificity for the melanoma antigen coupled to the dendritic cells in all the patients. However, there is the problem that tolerance to the injected peptide can be induced when the quantity of peptide is too low or when peptides have been modified with regard to their binding strength (J. Immunol. 1998, 160: 4449–56). As far as tumour therapy is concerned, this situation would be fatal; instead of immunizing the patient, this situation would cause the induced tumour antigens to be tolerated. Investigations carried out by the inventors have shown that the effect cannot be circumvented by injecting a relatively large quantity of dendritic cells, either. On the contrary, the degree of activation or maturation of the dendritic cells is a crucial factor in determining whether the use of these cells is likely to be successful.

A method for maturing dendritic cells using monocyte conditioned medium (MCM), tumour necrosis factor alpha (TNFα) or CD40 ligation is known from the prior art (J. Immunol. Methods 1996, 196: 121–135; J. Exp. Med. 1997, 185: 341–349; Blood 1998, 91: 4652–4661). In these methods, monocytes are isolated from peripheral blood and cultured with GM-CSF and IL-4. In order to complete the maturation of the cells into dendritic cells, additional cytokines have to be added at the end of the differentiation phase.

However, the methods which are known from the prior art suffer from a variety of disadvantages. The relatively long culture period is not suitable for hospital use. In addition, the high costs of the cytokines and the batch-dependence of the cytokines employed can be disadvantageous.

In the case of conventional vaccinations with antigens or peptides, there is also the problem that the immune response is frequently too weak or that, as mentioned above, the preparation of mature dendritic cells, which might be able to induce a better immune response, is too elaborate, too expensive and not sufficiently reproducible. In addition, it has been found, when vaccinating tumour patients, that, while immune responses can be elicited with a local antigen injection, these responses remain, to a large extent, restricted to the injected limb or even only to the closest lymph node station. There is, therefore, a need for a vaccination strategy, particularly for tumour patients, in whom the antigen can also be administered systemically in order to induce a generalized immune response. The most obvious solution to this problem, namely that of administering an intravenous dose of peptide and a suitable adjuvant, suffers from the disadvantage that, as a result of the dilution effect in the peripheral blood, the adjuvant becomes inactive in a very short period of time.

These problems can be solved on the basis of the surprising finding that low molecular weight hyaluronic acid fragments can be employed advantageously in different ways in immunotherapy, in particular for vaccinating tumour patients.

The present invention therefore makes available, in a general manner, the use of low molecular weight hyaluronic acid fragments, which can be suitably modified chemically, where appropriate, for producing a vaccine, in particular for vaccination by means of subcutaneous (s.c.), intracutaneous (i.c.) and intravenous (i.v.) vaccination, in particular for treating tumour patients.

In a first embodiment, the present invention makes available a process for concentrating mature dendritic cells, which process comprises the following steps:
 a) mononuclear cells are isolated from blood,
 b) cells which possess the CD14 surface marker are concentrated,
 c) the cells which possess the CD14 surface marker are cultured in a medium which contains the cytokines GM-CSF and IL-4, and
 d) the cells obtained in step c) are cultured together with hyaluronic acid fragments, which can be suitably modified, where appropriate, in order to induce the cells to mature into dendritic cells.

The invention likewise relates to vaccines which comprise the appropriately matured dendritic cells and to the use of the dendritic cells which have been matured with hyaluronic acid fragments for producing such vaccines.

In a further embodiment, the invention relates to vaccines which comprise low molecular weight hyaluronic acid fragments, which may be chemically modified, where appropriate, as adjuvant.

In a further embodiment, the invention relates to systems which contain an antigen or peptide, where appropriate together with a carrier system and, coupled to it, a low molecular weight hyaluronic acid fragment which can be suitably modified, where appropriate. In a further embodiment, the invention relates to vaccines which comprise an antigen or peptide which has been modified in this way with a hyaluronic acid fragment.

Particularly preferably, the vaccines according to the invention are used for subcutaneous (s.c.), intracutaneous (i.c.) or intravenous (i.v.) vaccination, in particular of tumour patients.

In that which follows, the first embodiment of the invention, namely the process for concentrating mature dendritic cells with hyaluronic acid fragments, which can be suitably modified, where appropriate, is described first of all, as are the corresponding vaccines which comprise these mature dendritic cells.

Mononuclear cells can be isolated from blood using a density gradient, with a leukocyte concentrate being fractionated through a Ficoll density gradient in a preferred embodiment.

In the second step of the process, the cells possessing the CD14 surface marker are concentrated, preferably using at least one antibody which is directed against the CD14 surface marker. Magnet-activated cell sorting (MACS) or fluorescence-activated cell sorting (FACS) can be employed in this connection. A simpler, but not so efficient method is that of enrichment by means of adhesion to plastic.

The cells possessing the CD14 surface marker are then cultured in a medium which contains GM-CSF at a concentration of from 5000 to 10000 U/ml and IL-4 at a concentration of from 100 to 1000 U/ml. Where appropriate, other suitable cytokines can also be added.

Finally, the cells which are obtained in the culturing step are cultured with hyaluronic acid fragments, with these fragments possessing from 1 to 50 basic building blocks of hyaluronic acid. A basic building block consists of an aminodisaccharide composed of D-glucuronic acid and N-acetyl-D-glucosamine which are linked by a $\beta$1-3 glycosidic bond. Preference is given to using hyaluronic acid fragments which each contain from 1 to 10 basic building blocks.

The cells possessing the CD14 surface marker are cultured in a medium containing GM-CSF and IL-4, preferably for a period of from at least 72 h up to 7 days. The cells are then cultured, in step d), with hyaluronic acid fragments for at least 48 hours. The hyaluronic acid fragments are preferably present at a concentration of from 1 to 50 $\mu$g/ml, and particularly preferably at a concentration of from 10 to 30 $\mu$g/ml.

Consequently, the present invention relates, in one embodiment, to the use of low molecular weight hyaluronic acid fragments for maturing dendritic cells.

The process according to the invention can be used to prepare and/or concentrate dendritic cells. The dendritic cells are antigen-presenting cells which are specialized for initiating the primary immune response. They assume different functions in the different stages of their development. In the immature state, dendritic cells are very efficient in processing native protein antigens for the MHC class II route. By comparison, mature dendritic cells are less suitable for taking up new proteins for presentation; on the other hand, they are much better at stimulating the growth and differentiation of resting CD4$^+$and CD8$^+$T cells.

In vivo, maturation of the dendritic cells begins when the immature dendritic cells migrate from the sites of antigen uptake to the T cell regions of the lymphoid organs. In vitro, it is possible to observe the maturation in cultures of freshly isolated dendritic cells. The maturation of the dendritic cells is also reflected in changes in morphology and phenotype. Dendritic cells are usually characterized and differentiated by detecting a variety of surface markers.

Because of their natural functions, dendritic cells are particularly suitable for being used as a natural adjuvant in vaccination and immunotherapy, in particular in tumour therapy. In this connection, it is of crucial importance, when the cells are being employed to achieve the sought-after therapy, to use fully matured DCs, which are unable to differentiate back, once again, into macrophage-like precursors following reinfusion into the patient.

According to the current state of knowledge, it is assumed that the dendritic cells take up the antigen (for example a tumour antigen) when they are in the immature state and then process the antigen. In connection with doing this, the dendritic cells mature and migrate to the T-cell-rich regions of the secondary lymphoid organs. Mature dendritic cells express large numbers of MHC molecules, costimulatory molecules and adhesion molecules on their surfaces, which molecules enable the dendritic cells to interact with the T cells (T cell clustering). Costimulatory signals are transmitted by way of B7-CD28 and CD40-CD40-ligand interactions, and are amplified by the production of cytokines, such as IFN-$\alpha$, IFN-$\gamma$ and IL-12, which, as is known, promote cell-mediated immunity.

According to the current state of knowledge, it appears to be essential for specialized antigen-presenting cells to be present for inducing a primary T cell response, since presenting antigens to T cells in the absence of a second signal (costimulation) may either cause the T cells to die or produce antigen-specific tolerance.

The advantages of the process according to the invention are therefore to be seen, in particular, in the fact that the dendritic cells can be prepared relatively simply. In addition, it is only necessary to use relatively low concentrations of expensive cytokines. The process according to the invention makes it possible to prepare a cell population which consists to a very large extent of dendritic cells, with these cells being in a relatively uniform (synchronous) state of maturity. When the dendritic cells are to be used for presenting antigens, the appropriate antigens can be added to the dendritic cells at a suitable time and the antigens can then be processed by the dendritic cells during the course of the maturation process. The antigens can be added as proteins, in the form of killed cells or cell preparations, or in the form of recombinantly modified cells. When the dendritic cells are in the desired state, they can then be used for the therapy.

The process according to the invention is suitable for preparing autologous dendritic cells. The term "autologous" means that the starting cells are taken from a donor (patient). These cells are then treated in accordance with the invention in vitro in order to obtain dendritic cells. The concentrated dendritic cells are then, where appropriate after contact with the antigen, readministered to the same donor from whom they were originally derived.

Alternatively, the process can also be used for preparing "allogenic" dendritic cells. In this case, the cells are prepared from a donor, or else from stored blood, which can be obtained from blood donor centres, and then readministered, in this case to other recipients. This makes it possible to prepare standardized dendritic cells which are, for example, optimally loaded with a tumour antigen. In this way, it is possible to increase cellular immunity efficiently, in particular in association with viral infection (HIV).

According to the invention, fragments of hyaluronic acid (HA), which may, where appropriate, be suitably modified, are employed for maturing the dendritic cells. Hyaluronic acid is a macromolecular polysaccharide which, as an endogenous substance, is used, first and foremost, in the corium for storing water. Hyaluronic acid is produced, in particular, by keratinocytes in the basal layers of the epidermis and by fibroblasts present in the subcutaneous connective tissue. Hyaluronic acid is also present in the vitreous humour of the eye and in the synovial fluid of the joints and is a constituent of connective tissue. At low concentrations, hyaluronic acid forms a highly viscous aqueous solution.

Hyaluronic acid is a high molecular weight compound having a molecular weight of between 50000 daltons and several million daltons. The basic building block of hyaluronic acid is an aminodisaccharide which consists of D-glucuronic acid and N-acetyl-D-glucosamine which are linked by a β1-3 glycosidic bond. This basic building block is linked to the next unit by a β1-4 glycosidic bond. This unbranched hyaluronic acid chain consists of from about 2000 to 10000 of such basic units. Hyaluronidases hydrolyse the β-glucosidic bonds and the hyaluronic acid is in this way broken down into smaller fragments. According to the invention, preference is given to using hyaluronidase from bull testes or the hyaluronidase which is isolated from Streptococcus hyaluronicus. The hyaluronic acid fragments which are employed in accordance with the invention are preferably first of all comminuted mechanically by shearing forces and/or ultrasonication, after which the polysaccharides are subjected to further degradation using a suitable hyaluronidase. The desired fragments, preferably consisting of from 1 to 50 basic units, are then isolated using suitable separation methods.

The hyaluronic acid fragments can be suitably modified chemically either before or after isolation. Preference is given to modifying them after isolation. Examples of modifications which may be mentioned are esterification, salt formation, amidation, reduction of an acid group to the aldehyde or alcohol, or elimination of an acid group. Salts and esters of the hyaluronic acid fragments, for example alkali metal salts and alkaline earth metal salts, and $C_1$–$C_{10}$-alkyl esters, preferably $C_1$–$C_4$-alkyl esters, are preferred. Other chemical modifications are also possible and can be effected by a skilled person, without difficulty, on the basis of his specialist knowledge.

The present invention is explained in more detail with the aid of the examples which are described below. In carrying out the examples, particular attention was paid to avoiding contamination of the reagents with lipopolysaccharides (LPS). Lipopolysaccharides are constituents of the cell walls of Gram-negative bacteria. Even the smallest contamination with lipopolysaccharides is sufficient to activate monocytes or $CD14^+$ stem cells present in the peripheral blood irreversibly. Care was therefore taken, in the experiments carried out in accordance with the invention, to keep below a threshold value of 0.01 ng of lipopolysaccharide/ml, below which value lipopolysaccharide has been found by experience not to have any effect on monocytes, $CD14^+$ stem cells or dendritic cells.

EXAMPLE 1
Cell Isolation
a) Isolating Mononuclear Cells (PBMC)

A leukocyte concentrate (buffy coat) from a healthy human donor was fractionated by centrifuging it through a density gradient containing Ficoll-Hyperpaque plus (Pharmacia, Uppsala, Sweden). Under these conditions, the mononuclear cells (PBMC) come to lie in the interphase zone of the gradient while red blood cells (erythrocytes) and neutrophilic granulocytes are to be found below the gradient, and are subsequently discarded. While Ficoll-Hyperpaque plus is a mixture of macrmolecular sugars of cellular origin, its LPS content is tested by the manufacturer (endotoxin content<0.001 ng/ml). This value was confirmed in our own tests.
b) Labelling the CD14-positive Cells In order to purify the monocytes still further, the PBMC were incubated for 45 min with anti-CD14 Mab. After that, they were washed with PBS and the cell pellet was resuspended in 2 ml of MACS buffer. MACS® (Miltenyi, Biotech, Bergisch Gladbach)=magnetic-activated cell sorting; a method for purifying cells using antibodies which are bound to metal beads; labelled cells remain suspended in the magnetic column matrix. [(PBS w/o $Ca^{2+}/Mg^{2+}$ (Gibco) containing 5 mM ethylenediaminetetraacetic acid (EDTA) and bovine serum albumin (BSA); pH adjusted to 7.2 by adding HCl]. Adding EDTA prevents the cells from clumping, something which is an important prerequisite for the purification in the column. The cells were now incubated, under the same conditions, with 50µl of goat anti-mouse IgG microbeads and then washed with MACS buffer, centrifuged and resuspended in 5 ml of MACS buffer.
c) Concentrating the CD14-positive Cells Using MACS The concentration took place at 4° C. The VS+® column was inserted in the MACS magnets (both from Miltenyi) and first of all washed with 5 ml of MACS buffer. In order to obtain a single-cell suspension, the cells were passed through a cell strainer (30 µm mesh width; Miltenyi) and loaded onto the column. The negative fraction, consisting of unlabelled cells which were not retained magnetically in the column matrix, passed through and were discarded. The column was washed a further two times with 5 ml of MACS buffer on each occasion in order to obtain a positive fraction which was as pure as possible. The column was then removed from the magnets and the cells which were retained in the matrix specifically by means of microbeads were washed, under pressure and using 5 ml of buffer, into a sterile tube. The cells which were obtained were counted in a Neubauer chamber. As a rule, it was possible, using this method, to obtain $3-5 \times 10^7$ CD14-positive cells (monocytes), at a purity of >90%, from one buffy coat. These cells can be completely converted into DC by adding cytokine.

EXAMPLE 2
Cell Culture

The isolated CD14-positive cells were taken up in 12 ml of c-RPMI [(cRPMI: "RPMI 1640" (Gibco, Paisley, Scotland) containing 10% heat-inactivated foetal calf serum, 1% L-glutamine and 1% penicillin/streptomycin); all the constituents contain less than 0.025 international endotoxin unit/ml (guide value for water for injection)]. In order to allow the cells to mature into dendritic cells (DCs), human GM-CSF for clinical use (Leukomax 400®, Sandoz AG, Nuremberg) and IL-4 (Genzyme, Rüisselsheim, batch tested for its LPS content: <0.001 ng/ml) were added to them at concentrations of 8000 units/ml of medium and 500 units/ml of medium, respectively. The cell suspension was then pipetted into a six-well plate at the rate of 2 ml per well and cultured in an incubator at 37° C. and 5% $CO_2$. On the fourth day, a further 2 ml of c-RPMI containing GM-CSF and IL-4 were added to each well.

EXAMPLE 3
Hyaluronic Acid Preparations
a) Fractionating Hyaluronic Acid and Separating Fragments Purified cockscomb hyaluronic acid (HA) (Healon®; Pharmacia, intended for clinical use, endotoxin content<0.001 ng/mg) was first of all cleaved into relatively large fragments using an ultrasonicator (Branson Sonifier) for 2 min. Hyaluronidase (Type I from bull testes; Sigma) was then added to the fragments in order to break them down still further. The reaction solution was adjusted to pH 5 with sodium acetate and incubated at 37° C. for 12 hrs; the hyaluronidase was then inactivated by heating at 90° C. The resulting fragments were then separated on the basis of their size. For this, they were layered on a polyacrylamide gel (Bio-Gel P-10, Bio-Rad, Munich) in a 1.5 m-long glass column. Double distilled water was used as the washing liquid, and a fraction collector (Pharmacia) below the column collected fractions every 20 min. The tubes were sealed and stored cool and protected from light.

b) Detecting the Sizes of the Hyaluronic Acid Fragments

1. Relatively large fragments obtained following ultrasonication size reduction

Sonicated HA was fractionated by gel electrophoresis in a 5% agarose gel. The polysaccharide bands in the gel were visualized by staining with Stains-all (3,3'-diethyl-9-methyl-4,5,4',5'-dibenzo-thiacarbocyanine; Sigma). The fragments obtained in this way are from 10000 to 50000 kDa in size.

2. Small fragments obtained following additional digestion with hyaluronidase ANTS labelling:

First of all, the individual samples had to be labelled with the fluorophore ANTS [ANTS solution: 0.15 M 8-aminonaphthalene-1,3,6-trisulphonic acid disodium salt in acetic acid/water (3/17, v/v), dissolved by slowly heating to 60° C.]. ANTS labels each sugar molecule at the end of the chain. The small fragments were likewise fractionated by gel electrophoresis using a 30% acrylamide gel. It was then possible to visualize the gel, and record it photographically, under UV light (ANTS dye).

c) Quantitatively Determining the Hyaluronic Acid Concentration After the Fragmentation and Separation 0.1 ml was withdrawn from each sample and mixed, in an icebath, with 0.6 ml of staining solution (5.2 g of disodium tetraborate in 1 l of concentrated sulphuric acid). 0.02 ml of Lipopolysaccharides (LPS) obtained from *Escherichia coli* serotype 0177 (Sigma) were used as the positive control.

Results:

1) Separating the resulting fragments by gel electrophoresis and ANTS staining. The fragments which are used in accordance with the invention are from 2 up to 12 sugar molecules in size. The concentration measurement gave values of about 1 mg of cleaved HA/ml. In principle, it is possible to cleave this fraction further into individual sugars by means of HPLC (high pressure liquid chromatography). The results lead to the conclusion that it is particularly the small fragments which are responsible for the stimulation.

2) Effect of the stimulation of DC by HA fragments on the expression of surface markers.

Antibodies can be used to establish the surface density of various receptors using the FACS images. Integrating the areas under the curves gives the so-called MFI (mean fluorescence intensity) value. These values are listed for various receptors in Table 1.

TABLE 1

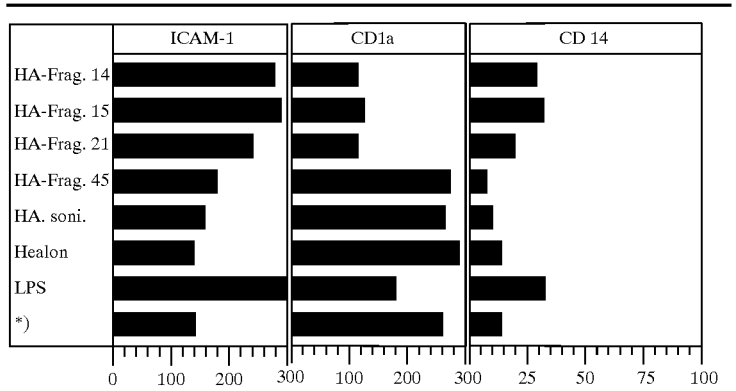

*) Untreated immature DCs, day 4

0.1% carbazole in ethanol was then added in each case and the reaction components were mixed and boiled again for 10 min. After the reaction mixtures had cooled down to room temperature, the HA concentration was determined photometrically at 520 nm. Distilled water was used for the blank value, while 0.2 µmol of HA/ml in distilled water was used as the standard.

EXAMPLE 4

Cell Stimulation

In order to stimulate the cells, different HA fragments were added to them, at a concentration of 0.025 mg/ml (25 µg/ml) of medium, on the fourth day of the culture.

Regarding the importance of the individual surface markers cited in Table 1:

ICAM-1 is an intercellular adhesion molecule which occurs almost ubiquitously. The results show a slight up-regulation, as is observed in very many different types of cell activation. CD1a is a marker for dendritic cells and Langerhans cells of the skin; while monocytes only express CD14, there is an ever increasing loss of CD14, and expression of CD1a, during the course of the maturation. While LPS, HA fragments and MCM medium suppress this process to a slight extent, the functional consequences of this regulation are unknown.

TABLE 2

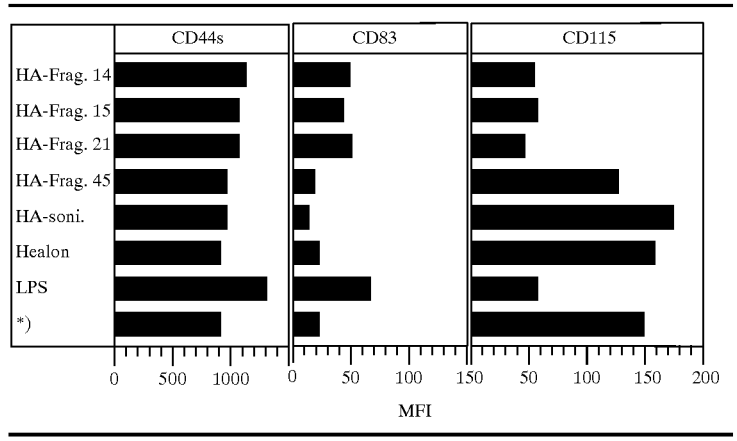

*) Untreated immature DCs, day 4

Table 2 shows the stimulation of other surface markers (CD44s, CD83 and CD115). While a further sign of DC maturation is a downregulation of CD115 (the G-CSF receptor) and an up-regulation of CD83, the functional relevance of these changes is still not known. It can be clearly seen from Table 2 that the criteria of DC maturation by stimulation with small HA fragments are fully met.

CD44 is an adhesion molecule, a reported function of which is that of binding HA.

TABLE 3

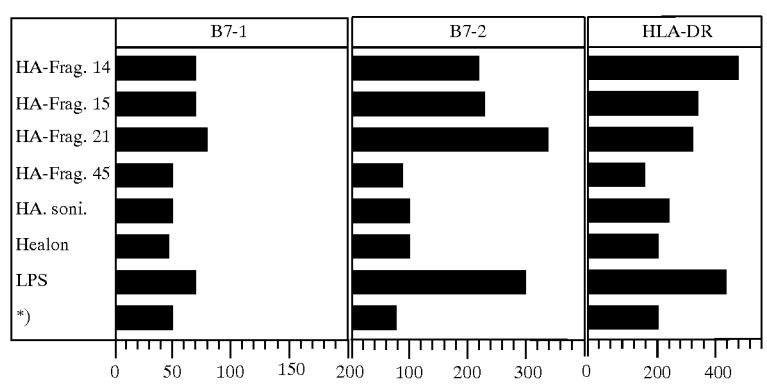

*) Untreated immature DCs, day 4

Table 3 shows the expression of other surface markers.

This table depicts factors, apart from maturation markers, which play a crucial role for the function of the cells in antigen presentation, i.e. in stimulating T lymphocytes. These factors include the MHC class II molecule HLA-DR and the two costimulatory factors B7-1 and B7-2. Without these factors being up-regulated, there would be no point, either, in using DCs for the above-described applications. According to the invention, a marked up-regulation of all the factors was found after treatment with HA fragments, with this up-regulation being comparable with the maximum stimulation achieved following the addition of LPS.

EXAMPLE 5

In order to portray the increased expression of surface molecules in a functional manner, the DCs were prestimulated and then incubated for 5 days with purified, naive allogenic T cells which had likewise been obtained from leukocyte concentrate (buffy coats) (so-called mixed leukocyte reaction, MLR). Under these conditions, the T cells proliferated, as measured by the incorporation of radioactive $^3$H-thymidine, with this proliferation being more or less pronounced depending on the stimulatory capacity of the DCs. The radioactive counts per minute (cpm) in the individual samples, which counts correlate directly with the T cell proliferation which occurred, are given in Table 4. It can be seen that DCs which were treated with small HA fragments are markedly more potent APCs, with the values for these DCs being comparable with that obtained for LPS stimulation (shown in Table 4 B).

This example, too, provides evidence that a marked maturation of DCs is obtained when small HA fragments, of between 2 and 12 UDP-sugar molecules, are used in accordance with the invention, with this maturation being entirely comparable with published data from other methods. While strict dependence on a single sugar appears to be unlikely, larger molecules (20–30 UDP-sugars) evidently have no influence since the fractions which are used in accordance with the invention do not exhibit any differences in their effect even when they contain larger fragments. Sonicated HA does not have any effect, either.

EXAMPLE 6

Interestingly, the effect according to the invention is evidently specific for DCs, since gamma interferon (IFNγ)-treated monocytes, which mature into macrophages, do not exhibit any increase in their stimulatory capacity following treatment with HA fragments (see Table 4 A).

TABLE 4

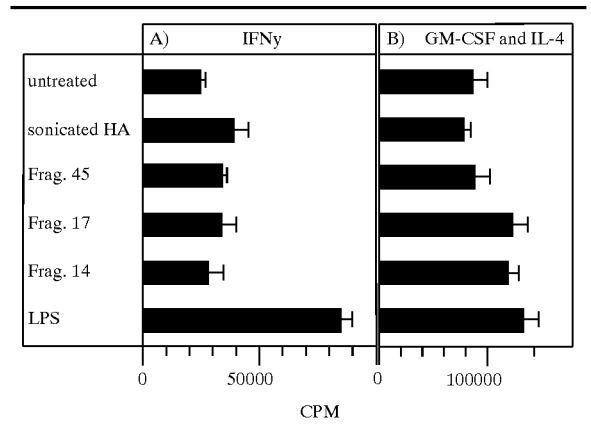

Frag. 45: No detection of small HA fragments in gel electrophoresis; in the uronic acid assay, less than 0.001 mg of HA=negative fraction for excluding an effect of column constituents.

Frag. 17: In gel electrophoresis, the largest detectable bands are at approx. 16-fold sugars; sugars having a size of up to 6-fold sugars are strongly represented. Uronic acid assay: 1 mg/ml.

Frag. 14: Gel electrophoresis: up to approx. 22-fold sugars, strong bands up to 10-fold sugars; uronic acid assay: 1 mg/l.

EXAMPLE 7

In this example, it is shown that dendritic cells which have been matured with low molecular weight hyaluronic acid fragments are surprisingly superior to conventional dendritic cells in inducing a peptide-mediated, hapten-specific immunity.

Mice (C57/BL6, female, 6–12 weeks, 60 animals, 5 mice per experimental group, 20 g per mouse) were injected with dendritic cells which had previously been treated with a synthetically prepared protein having a defined amino acid sequence, i.e. a (SIINFEK*L (SEQ ID NO: 1), SIIK*FEKL (SEQ ID NO: 2); *=TNP lysine) peptide. The peptide is selected such that it can react directly with the MHC molecule antigen-binding site on the cell surface of antigen-presenting cells; this means that it is presented on the surface of dendritic cells immediately after they have been added. The hapten trinitrophenyl (TNP), which constitutes the antigenic determinant, is in turn coupled to this peptide. This means that a T cell which is activated by the trinitrophenyl-coupled peptide which is presented by the dendritic cell becomes reactive to trinitrophenyl or chemicals which are structurally homologous to trinitrophenyl, such as the trinitrochlorobenzene (TNCB) used during the challenge which is implemented below. Accordingly, in this system, the strength of the trinitrophenyl-specific T cell reaction depends on the degree to which the dendritc cells are activated and/or the efficiency with which the trinitrophenyl-coupled peptide is presented to the T cells by the dendritic cells. The method is a recognized model for the in-vivo investigation of mechanisms which play a role during T cell activation.

Appropriate methods are more precisely described, for example, in the publications J. Invest. Dermatol. 1998, 110: 441–48; Eur. J. Immunol. 1995, 25: 92–101 and J. Immunol. 1993, 151: 678–87.

The injected dendritic cells induce a T cell-mediated immune response within a week. That is, after having been injected, they migrate into the lymphatic organs and induce the above-described T cell activation in these organs. After this period of time, the efficiency of the immunization which has been effected can be quantified with the aid of an ear swelling reaction, which is induced by directly applying (painting the ear with a 1% solution of TNCB) a trinitrophenyl analogue, in our case trinitrochlorobenzene (TNCB) to the ear. Within 24 h, this treatment induces an inflammation reaction whose strength depends on the number of memory T cells present in the skin. The ear swelling reaction is measured as the increase in thickness of the ear in $\mu$m. The results are summarized in Table 5 below.

TABLE 5

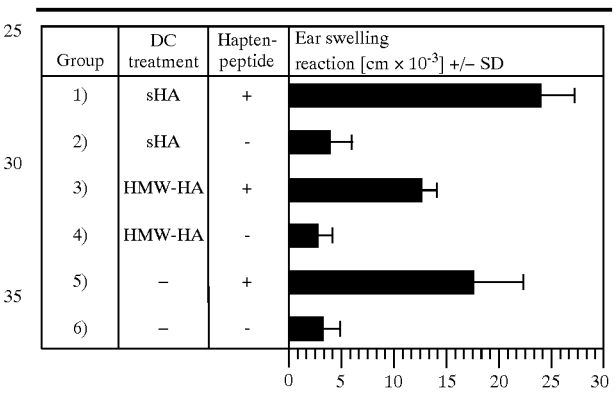

In this system, a marked increase in the ear swelling reaction was detected after the dendritic cells had been pretreated with low molecular weight hyaluronic acid fragments. The injection of untreated dendritic cells (group 6) scarcely induces any detectable ear swelling reaction, as is also the case when the dendritic cells are only pretreated with high molecular weight hyaluronic acid (group 4) or low molecular weight hyaluronic acid fragments (group 2). When the dendritic cells are pretreated with hapten-peptide (group 5), a marked ear swelling reaction of approx. 0.15 mm then ensues. The T cell response can be significantly improved by additionally pretreating the dendritic cells with low molecular weight hyaluronic acid fragments, and then displays an ear swelling reaction of approx. 0.24 mm (group 1). On the other hand, pretreating the dendritic cells with high molecular weight hyaluronic acid and hapten-peptide (group 3) does not result in any significant improvement as compared with the untreated control group 5.

EXAMPLE 8

In this example, vaccinations with dendritic cells, which had been treated with low molecular weight hyaluronic acid fragments, were tested for their ability to induce antiviral immunity using a mouse model having specificity for lymphocytic chorio-meningitis virus (LCMV). The test method employed is known in principle from the publication J. Virol. 1998, 72: 3812–18.

In the same manner as described in Example 7, dendritic cells were treated, for this purpose, with GP-33, a peptide which encodes the antigenic determinant of a surface antigen of the LCM virus, and then injected into the mouse intravenously. As previously described, this immunizes the animal against LCMV, with the efficiency of the immunization depending on the degree of activation and/or the pretreatment of the dendritic cells. The efficiency of the immunization was then determined after a week by inoculating the mouse with the complete LCMV. Successful immunization against the virus can be deduced from a clonal expansion of GP-33-specific T cells in the blood and the lymphatic organs of the treated animals. In another assay, the virus load (number of viruses) is determined in the peripheral blood.

In a second embodiment, which will be described below, the invention makes available a vaccine which comprises at least one antigen or peptide and a low molecular weight hyaluronic acid fragment, which may be modified, where appropriate, as an immune response amplifier (adjuvant). Surprisingly, it has been found that low molecular weight hyaluronic acid fragments, which may be modified, where appropriate, can advantageously be used as an adjuvant when directly vaccinating with antigens or peptides.

In this method, a vaccine, which comprises the antigen, is injected into the patient subcutaneously (s.c.), intracutaneously (i.c.) or else intravenously (i.v.). The injected antigen is taken up by endogenous antigen-presenting cells (APC), e.g. the dendritic cells, and presented in the regional lymph nodes, thereby inducing an antigen-specific immune response. Surprisingly, it was possible to show that simultaneously injecting low molecular weight hyaluronic acid fragments, which can be chemically modified, where appropriate, amplifies the immune response by recruiting, activating and maturing APC at the puncture site.

The low molecular weight hyaluronic acid fragments, or their chemical modifications, have already been described in detail in the first embodiment of the invention. The low molecular weight hyaluronic acid fragments, or their chemical modifications, which can be employed in this second embodiment of the invention are the same as those described in the first embodiment. They are likewise prepared as described above.

In principle, the novel vaccine according to the second embodiment can comprise any antigen or peptide which is to elicit an immune response. The hyaluronic acid fragments, or the chemical modifications thereof, are preferably present in the same solution in which the antigen or peptide is also present. However, it is also possible to administer the antigen or peptide separately from the low molecular weight hyaluronic acid fragments or their chemical modifications. A vaccine which comprises both the antigen or peptide and the low molecular weight hyaluronic acid fragment, which can be chemically modified, where appropriate, comprises the antigen or peptide at a concentration of from approx. 1 to 1000 µg/ml, preferably at a concentration of from 10 to 100 µg/ml, and the low molecular weight hyaluronic acid fragment, or its chemical modifications, at a concentration of from 10 ng/ml to 1000 µg/ml, preferably at a concentration of from 10 µg/ml, to 100 µg/ml, e.g. 30 µg/ml. A suitable daily dose of antigen or peptide is, for example, from 1 to 1000 µg/day, preferably from 10 to 100 µg/day, and the daily dose of the low molecular weight hyaluronic acid fragments, or their chemical modifications, can, for example, be from 10 ng/day to 1000 µg/day, preferably from 10 µg/day to 100 µg/day, e.g. 30 µg/day.

Apart from the antigen or the peptides and the low molecular weight hyaluronic acid fragments, which can be chemically modified, where appropriate, the compositions according to the invention can also comprise other auxiliary substances which are known in the prior art, e.g. Freund's adjuvant.

According to the invention, the low molecular weight hyaluronic acid fragments, or their chemical modifications, can be administered and used in a manner which is customary in the field and with which the skilled person is familiar.

The following example explains this second embodiment of the invention.

EXAMPLE 9

In order to test the in-vivo activity of low molecular weight hyaluronic acid fragments, healthy test subjects (N=3) were injected subcutaneously with 100 µl of a 1 mg/ml preparation of low molecular weight hyaluronic acid fragments (one basic unit and fragments containing from 2 to 20 basic units) and, as control, 100 µl of isotonic sodium chloride solution (0.9% NaCl) on two consecutive days. On day three, punch biopsies were removed and the preparations were worked up immunohistologically. From the clinical point of view, a slight inflammatory reaction, in the form of a discrete reddening around the puncture site, appeared only 24 h after the subcutaneous injection of low molecular weight hyaluronic acid fragments, as did a marked infiltrate, which mainly consisted of activated, mature dendritic cells. The results obtained with the immunohistological preparations are summarized in Table 6. The cells infiltrating into the corium were counted under the microscope, at 40 times magnification, using a grid eyepiece; 3×12 fields were counted per preparation and the number of infiltrating cells per $mm^2$ were calculated from this. Table 6 shows the clear increase in infiltrating cells which took place only 24 h after injecting low molecular weight hyaluronic acid fragments; by contrast, the control injection, which was carried out in parallel, does not display any such effect. The precise immunophenotyping of the infiltrate shows a marked preponderance of CD1a and HLA-DR-positive cells at the sites treated with low molecular weight hyaluronic acid fragments, i.e. the cells display the phenotype of mature dendritic cells. It is not possible to observe any clear increase in lymphocytes or individual subclasses (CD19=B cell marker, CD3=T cell marker, CD4=T helper cell marker, CD8=labelled cytotoxic T cells) at least in the period over which the observation took place (Table 6). In marked contrast to this finding, the infiltrate obtained following the control injection of isotonic sodium chloride solution shows a substantially more homogeneous distribution, which is comparable to the distribution of the individual subclasses which is found in association with a non-specific inflammatory reaction (Table 6).

TABLE 6

| Period of observation | 24 h | 24 h | 48 h | 48 h |
|---|---|---|---|---|
| Agent | sHA frag. | 0.9% NaCl | sHA frag. | 0.9% NaCl |
| Infiltrating cells/$mm^2$ | 365 | 123 | 453 | 235 |
| CD1a-positive | 89% | 49% | 78% | 42% |
| HLA-DR-positive | 75% | 34% | 83% | 45% |
| CD3-positive | 23% | 44% | 28% | 52% |
| CD4-positive | 15% | 26% | 17% | 40% |
| CD8-positive | 6% | 8% | 8% | 15% |
| CD19-positive | 2% | 1% | 1% | 3% |

The example provides evidence that, in addition to potently activating dendritic cells in vitro, in accordance with the first embodiment of the invention, low molecular weight hyaluronic acid fragments are evidently also able to elicit a directed immigration of activated dendritic cells to the injection site in vivo. After having taken up coinjected antigen/peptides, or antigen-peptides which are coupled to low molecular weight hyaluronic acid fragments, these dendritic cells then migrate to the regional lymph nodes, where they are able to induce a specific T cell-mediated immune response.

The third embodiment of the invention, which makes available vaccines which comprise a system in which the low molecular hyaluronic acid fragments, or their chemical modifications, are coupled to an antigen or peptide, is described below. In particular, this embodiment of the invention solves the problem that, while immune responses can be induced by means of a local antigen injection, these responses remain, to a large extent, restricted to the injected limb or even only to the nearest lymph node station. When the novel vaccines according to the third embodiment are used, it is also possible to administer the antigen systemically, e.g. intravenously, without the adjuvant (the low molecular weight hyaluronic acid fragments which can be chemically modified, where appropriate) becoming inactive within a short period of time due to the dilution effect in the peripheral blood.

The low molecular weight hyaluronic acid fragments, or their chemical modifications, are the same as those which have already been described in the first embodiment and can be prepared in the same manner.

Antigens or peptides which are customarily employed in vaccines, preferably in vaccines for tumour therapy, may be mentioned as the antigen or peptide, where appropriate together with a carrier system.

The nature of the coupling between the low molecular weight hyaluronic acid fragment, which can be chemically modified, where appropriate, and the peptide or antigen, where appropriate together with a carrier system, is not restricted in any particular way. Preference is given to the coupling taking place by the chemical covalent bonding of the antigen or peptide to the adjuvant (low molecular weight hyaluronic acid fragment or chemical modification thereof) or by the antigen or peptide and the adjuvant being jointly included in a microsphere, as is described, for example, in Cancer Res. 1998, 58: 3385–90.

Particular preference is given to coupling the basic building block, UDP-β-D-N-acetylglucosamine, which is used in synthesizing hyaluronic acid, to the antigen or, preferably to the peptide. This means that particular preference is given, in the third embodiment of the invention, to the hyaluronic acid fragment which contains one basic unit. As has been previously explained, the basic unit is an aminodisaccharide composed of D-glucuronic acid and N-acetyl-D-glucosamine which are linked by a β1-3-glycosidic bond. UDP-β-D-N-acetylglucosamine is commercially available.

The vaccines in accordance with the third embodiment of the invention can be produced using methods and additives which are, in principle, known in the prior art. The only essential point is that use is made of the novel combinations of the peptide or antigen, where appropriate together with a carrier system, and the low molecular weight hyaluronic acid fragment, which can be chemically modified, where appropriate. It goes without saying that, in the present case, the chemical modification of the hyaluronic acid fragment can also be selected such that a suitable chemical coupling to the antigen or peptide can be effected advantageously. Suitable chemical modifications and coupling methods are known in principle to the skilled person, and any arbitrary methods of the prior art can be used.

A novel vaccine according to the third embodiment of the invention comprises, for example, from 1 μg/ml to 1000 μg/ml, preferably from 10 μg/ml to 100 μg/ml, of the antigen or peptide, where appropriate together with a carrier system. A suitable daily dose of antigen or peptide, where appropriate together with a carrier system, is, for example, from 1 μg/day to 1000 μg/day, preferably from 10 μg/day to 100 μg/day. If the coupling between the antigen or peptide and the low molecular weight hyaluronic acid fragment, or chemical modification thereof, has taken place by covalent bonding, the concentration or daily dose of the low molecular weight hyaluronic acid fragment, or of its chemical modification, is necessarily the same as the corresponding concentration or daily dose of the antigen or peptide, where appropriate together with a carrier system. If the low molecular weight hyaluronic acid fragment, which can be chemically modified, where appropriate, and the antigen or peptide are not bonded together chemically but, instead, are jointly included in a microsphere, for example, the preferred concentration of the low molecular weight hyaluronic acid fragment, or its chemical modification, is likewise preferably the same as the concentration of the antigen or peptide.

Possible additives for the vaccine are those additives which are generally customary, e.g. Freund's adjuvant. The vaccine is produced in a manner which is in principle known from the prior art.

The example explains the third embodiment of the invention.

EXAMPLE 10

In order to bring the vaccine peptide and the adjuvant as close together as possible, the low molecular weight hyaluronic acid fragment, or the basic building block, UDP-β-D-N-acetylglucosamine used in the hyaluronic acid synthesis (fragment containing one basic unit) was coupled directly to the peptide. UDP-β-D-N-Acetylglucosamine can be obtained as a pure substance from Oxford Glucosciences and exhibits an effect on dendritic cells which is similar to that exhibited by hyaluronic acid cleavage products both as regards the required concentration of the substance and as regards the degree of activation. The well-known conversion of aldehydes and amino groups to Schiff's bases is used for the coupling. A certain percentage of the sugar molecule is present in its open-chain aldehyde form and enters into the abovementioned reaction with the protein in aqueous solution.

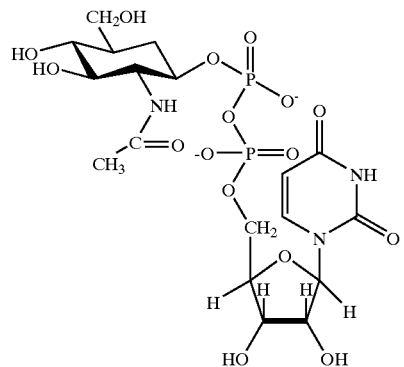

UDP-β-D-N-Acetylglucosamine

In order to stabilize the product, the compound is reduced by adding sodium borohydride (NaBH₄), thereby forming, with the elimination of water, a covalent bond between the carbon atom of the aldehyde group and the nitrogen atom of the amino group on the peptide.

In order to check its activity, the compound which has been prepared in this way can be administered either intracutaneously or subcutaneously in 50–100 µl of isotonic sodium chloride solution. As previously described, the peptide-HA compound binds to MHC molecules on the surface of antigen-presenting cells, e.g. dendritic cells, and should simultaneously activate the cells. The compound can also be administered intravenously.

Preferred examples of peptides against tumour antigen or virus antigen, which peptides are preferred in all the embodiments according to the invention, are listed in Table 7:

TABLE 7

| Antigen name: | Peptide sequence: | Target cell: |
|---|---|---|
| MELAN-1/MART-1 | EAAGIGILTV (SEQ ID NO: 3) | human melanoma |
| Tyrosinase | AFLPWHRLFL (SEQ ID NO: 4) | human melanoma |
| GP-33 | KAVYNFATM (SEQ ID NO: 5) | LCM virus |

The novel vaccines according to all the embodiments can comprise the antigen or peptide, where appropriate together with a suitable carrier system as well. Examples of these carrier systems are liposomes and microsomes, which, as is known from the prior art, can be prepared from phospholipid compounds.

What is claimed is:

1. A composition comprising dendritic cells prepared by:
   (a) isolating mononuclear cells from blood
   (b) culturing said mononuclear cells, together with hyaluronic acid fragments, in order to cause said mononuclear cells to mature irreversibly into said dendritic cells,
   wherein each of said hyaluronic acid fragments is from 2,000–5,000 Da.

2. The composition of claim 1, further comprising an acceptable excipient.

3. A process for maturing dendritic cells, comprising:
   (a) isolating mononuclear cells from blood
   (b) culturing said mononuclear cells, together with hyaluronic acid fragments, in order to cause said mononuclear cells to mature irreversibly into said dendritic cells,
   wherein each of said hyaluronic acid fragments is from 2,000–5,000 Da.

4. The process of claim 3, wherein said mononuclear cells are isolated from a leukocyte concentrate using a density gradient.

5. The process of claim 4, wherein said density gradient is a Ficoll density gradient.

6. The process of claims 3, wherein said mononuclear cells possess a CD14 surface marker and are further concentrated, after isolation from said leukocyte concentrate, using an antibody that is directed against said CD14 surface marker.

7. The process of claim 3, wherein said mononuclear cells possess a CD14 surface marker and are cultured in a medium that contains GM-CSF at a concentration from 5,000 to 10,000 U/mL and IL-4 at a concentration from 100 to 1,000 U/mL.

8. The process of claim 3, wherein said hyaluronic acid fragments each contain from 1 to 10 aminodisaccharides.

9. The process of claim 3, wherein said mononuclear cells possess a CD14 surface marker and are cultured for 72 hours to 7 days in a medium containing GM-CSF and IL-4.

10. The process of claim 3, wherein said mononuclear cells are cultured together with said hyaluronic acid fragments for at least 48 hours.

11. The process of claim 3, wherein said hyaluronic acid fragments are chemically modified.

12. The process of claim 3, wherein said hyaluronic acid fragments are present at a concentration of 30 to 50 µg/ml.

* * * * *

SEQUENCE LISTING

```
<160> NUMBER OF SEQ ID NOS: 5

<210> SEQ ID NO 1
<211> LENGTH: 9
<212> TYPE: PRT
<213> ORGANISM: Artificial Sequence
<220> FEATURE:
<223> OTHER INFORMATION: Synthetic protein
<221> NAME/KEY: MOD_RES
<222> LOCATION: (8)..(8)
<223> OTHER INFORMATION: Xaa is trinitrophenyl lysine

<400> SEQUENCE: 1

Ser Ile Ile Asn Phe Glu Lys Xaa Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic protein
<221> NAME/KEY: MOD_RES
<222> LOCATION: (5)..(5)
<223> OTHER INFORMATION: Xaa is trinitrophenyl lysine

<400> SEQUENCE: 2

Ser Ile Ile Lys Xaa Phe Glu Lys Leu
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide

<400> SEQUENCE: 3

Glu Ala Ala Gly Ile Gly Ile Leu Thr Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide
```

```
-continued

<400> SEQUENCE: 4

Ala Phe Leu Pro Trp His Arg Leu Phe Leu
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Lys Ala Val Tyr Asn Phe Ala Thr Met
1               5
```